United States Patent
Eschenmoser

[11] 3,939,207
[45] Feb. 17, 1976

[54] METHOD FOR PREPARING ALDEHYDES
[76] Inventor: Albert Eschenmoser, Bergstrasse 9, Kuesnacht, Zurich, Switzerland
[22] Filed: Mar. 16, 1973
[21] Appl. No.: 341,829

Related U.S. Application Data
[63] Continuation-in-part of Ser. No. 856,478, Sept. 9, 1969, abandoned.

[30] Foreign Application Priority Data
Sept. 19, 1968 Switzerland............ 14014/68

[52] U.S. Cl............ 260/601 R; 260/239 E; 260/598
[51] Int. Cl.²........................................ C07C 47/20
[58] Field of Search.................... 260/598, 601 R

[56] References Cited
UNITED STATES PATENTS
3,210,396  10/1965  Horvitz ............................ 260/458
3,835,160   9/1974  Tanabe ............................ 260/340.9

OTHER PUBLICATIONS
Felix et al., Helvetica Chim. Acta, 51, 1461 (1968).

Primary Examiner—James O. Thomas, Jr.
Assistant Examiner—Nicky Chan
Attorney, Agent, or Firm—Joseph G. Kolodny; Theodore O. Groeger; John J. Maitner

[57] ABSTRACT
A process for the manufacture of aldehydes of the general formula

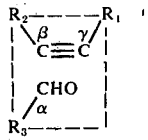

in which the symbols $R_1$, $R_2$ and $R_3$ stand for hydrogen or organic radicals and in which at least two of these radicals are linked together by fragmenting a corresponding aziridine compound of the general formula

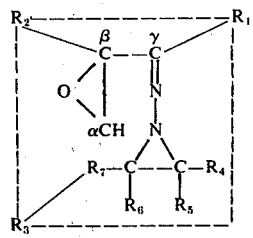

in which $R_1$, $R_2$ and $R_3$ are as above and $R_4$ to $R_7$ each represents hydrogen, an alkoxycarbonyl, cyano, nitro or sulphonyl group or an alkyl, alkenyl, cycloalkenyl or alkyl residue and two or more of these residues may be linked together with simultaneous evolution of nitrogen.

13 Claims, No Drawings

METHOD FOR PREPARING ALDEHYDES

CROSS REFERENCES TO RELATED APPLICATIONS

This is a continuation-in-part of application Ser. No. 856,478, filed Sept. 9, 1969 (now abandoned). Application Ser. No. 679,200, filed Oct. 30, 1967 discloses a process for the manufacture of α-oxo-α,β-seco-β(γ)-acetylene compounds of the general formula (I)

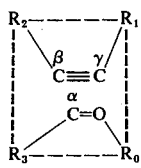

in which $R_{1-3}$ and $R_0$ each represents hydrogen or an organic residue and at least two of these residues are linked together, characterized in that a compound of the general formula (II)

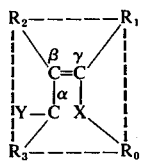

in which $R_{1-3}$ and $R_0$ have the above meanings, X represents a diazonium residue or a residue which can be converted into a diazonium residue under the decomposition conditions, and Y represents a residue convertible into an oxo group under the reaction conditions and by a possibly following hydrolysis, is decomposed with fragmentation and elimination of molecular nitrogen, and the resulting product, if desired, is hydrolyzed. The said specification describes more especially the fragmentation, accompanied by development of nitrogen of α,β-oxido-γ-carbonyl compounds of the formula (III)

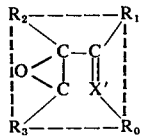

in which X' represents a nitrogenous derivative of an oxo group, such as the oximido group or a derivative thereof esterified or etherified on the oxygen, or a hydrazino group or a derivative thereof substituted by a nucleofuge group, or an iminoaziridine group. This process is specially concerned with the manufacture of cycloaliphatic α-oxo-α,β-seco-β(γ)-acetylene compounds and of α-oxo-α,β-seco-steroid-β(γ)-ines.

SUMMARY OF THE INVENTION

The present invention is based on the observation that the fragmentation of compounds of the formula II, in which $R_0$ represents a hydrogen atom, can be achieved especially easily and with particularly good yields via the iminoaziridine derivatives.

Accordingly, the present invention provides a process for the manufacture of aldehydes of the general formula (IV)

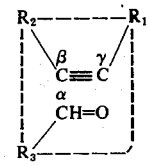

in which $R_{1-3}$ have the above meanings, which is characterized in that an iminoaziridine compound of the general formula (V)

![](formula V)

in which $R_{1-3}$ have the above meanings and $R_{4-7}$ each represents hydrogen, an alkoxycarbonyl, cyano, nitro or sulphonyl group or an alkyl, alkenyl, cycloalkyl or aryl residue, and two or more of these residues may be linked together, is fragmented with development of nitrogen.

This fragmentation of the epoxy-iminoaziridine is accompanied by elimination of molecular nitrogen, splitting of the bond between carbon atoms α and β and formation of a triple bond between carbon atoms β and γ and of an oxo group on carbon atom α, according to the general scheme (V) → (IV)

DESCRIPTION OF THE PREFERRED EMBODIMENTS

The starting materials to be used in the present process are derived from α,β-epoxy-carbonyl compounds of the general formula (VI)

in which $R_{1-3}$ each represents a hydrogen atom or an organic residue, preferably at least one of these symbols representing one of the following residues:

a. a saturated or unsaturated acyclic hydrocarbon residue, being a linear or branched carbon chain, possibly interrupted by hetero atoms, which may contain at least one functional group, or b. a saturated or unsaturated mono- or polynuclear alicyclic hydrocarbon residue which may be nucleus-substituted, or c. a mono- or polynuclear aromatic hydrocarbon residue which may be substituted on the nucleus, or d. a mono- or polynuclear aralkyl or aralkenyl residue which may be nucleus-substituted, or e. a saturated or unsaturated, mono- or polynuclear heterocyclic residue which may be nucleus-substituted and at least two of the symbols $R_{1-3}$ together may represent atomic groups which together with carbon atoms $\alpha$ and/or $\beta$ and/or $\gamma$ form saturated or unsaturated, mono- or polynuclear carbocycles or heterocycles which may be substituted on the nucleus.

The organic residues mentioned above may contain additional functional groups.

Preferred starting materials are, for example, compounds derived from the following $\alpha,\beta$-epoxyketones:

a. $\alpha,\beta$-Epoxycarbonly compounds containing a carbocycle or heterocycle which preferably contains 5 or more cyclic members, in which the epoxide group is attached to vicinal carbon atoms of the ring, of which one carries a hydrogen atom and the carbonyl group is in a side-chain in $\alpha$-position to the epoxide group. The ring may be condensed on carbon atoms that do not belong to the epoxide group, with a further mono- or polycyclic carbocyclic and/or heterocyclic system. The ring or rings may contain substituents, for example hydrocarbon residues which may carry functional groups or be substituted by functional groups. The side-chain carrying the carbonyl group may be especially a hydrocarbon residue with one or several carbon atoms which may be interrupted by hetero atoms, for example oxygen, sulphur or nitrogen, it may contain one or several unsaturated carbon-to-carbon bonds and may carry in addition to the carbonyl group further functional groups. The starting materials derived from the said carbonyl compounds furnish on fragmentation according to the present process either open-chain compounds containing a carbonyl group and a triple bond, or cyclic compounds in which the newly formed carbonyl group and the triple bond are separately located in two side-chains. As examples of carbonyl compounds of this kind there may be mentioned the following:

1-(1-oxo-5-ethyl-hept-4-en-1-yl)-1,2-epoxy-cyclopentane, 1-propionyl-1,2-epoxy-cyclohex-4-ene, 1-formyl-1,2-epoxy-cyclooctane and epoxy-cedrenal.

b. $\alpha,\beta$-Epoxyketones containing a carbocycle or heterocycle which preferably contains 8 or more cyclic members, in which the keto group is situated in the ring and the epoxide group exocyclically in a side-chain in $\alpha$-position to the keto group. The ring may be condensed with a further mono- or polycyclic carbocycle and/or heterocycle. The ring or rings may contain substituents, for example functional groups or hydrocarbon residues which may carry functional groups. The side-chain containing the epoxide group may be primarily a hydrocarbon residue with 1 or more carbon atoms, which may be interrupted by hetero atoms, for example oxygen, sulphur or nitrogen, may contain one or several further unsaturated carbon-to-carbon bonds and functional groups. The starting materials derived from these carbonyl compounds furnish on fragmentation by the present process two scission products, namely a cyclic compound containing a triple bond, and an open-chain carbonyl compound. As an example of a cyclic ketone of this group 2-benzyl-2,1'-epoxy-cyclopenta-decan-1-one may be mentioned.

c. $\alpha,\beta$-Epoxyketones with a carbocycle or heterocycle which preferably contains 5 or more cyclic members, in which the keto group as well as the epoxide group are located in the ring. The ring may be condensed on carbon atoms that belong neither to the epoxide group nor to the keto group with a further mono- or polycyclic carbocycle and/or heterocycle. The ring or rings may contain substituents, for example functional groups or hydrocarbon residues which may carry functional groups. The starting materials derived from carbonyl compounds of this group furnish on fragmentation according to the present process either open-chain compounds with an aldehyde group and a triple bond, or cyclic compounds in which the aldehyde group and the triple bond are located in two different side-chains. As examples of carbonyl compounds of this group the following compounds may be mentioned:

2-ethyl-2,3-epoxy-cyclopentan-1-one,
2-buytl-2,3-epoxy-cyclopentan-1-one,
2-pentyl-2,3-epoxy-cyclopentan-1-one,
2-hexyl-2,3-epoxy-cyclopentan-1-one,
2-heptyl-2,3-epoxy-cyclopentan-1-one,
2-(4-methyl-pent-3-en-yl-[1])-2,3-epoxy-cyclopentan-1-one,
2-decyl-2,3-epoxy-cyclopentan-1-one,
2-methyl-2,3-epoxy-cyclohexan-1-one and
2-(dec-4-en-yl[1])-2,3-epoxy-cyclohexan-1-one.

Starting materials derived from the carbonyl compounds of groups (a), (b) and (c) furnish by the present process acetylene compounds which may be used in a variety of ways as intermediates in the manufacture of technically valuable known and new compounds. Those acetylene compounds which simultaneously contain a carbonyl group may be converted into known or new aromas or flavours, for example by catalytic partial or total hydrogenation.

As preferred starting materials there may be further enumerated those which are derived from $\alpha,\beta$-epoxy-$\gamma$-oxosteroids whose epoxide group is attached to vicinal carbon atoms of the steroid ring skeleton and whose $\alpha$-carbon atom does not at the same time belong to two rings.

They belong especially to the androstane, pregnane, cholane, cholestane, spirostane, furostane or cardanolide series or their A-nor, A-homo, B-nor and/or B-homo derivatives or their 19-nor derivatives, for example to the oestranes and they contain the oxo group in one of the positions 1,2,3,4, 15, 17 or 20. In the first place starting materials are used that are derived from 3-oxo-1,2-epoxy-steroids, 4-oxo-2,3-epoxy-steroids or from 20-oxo-16,17-epoxy-steroids of the series referred to above.

Preferred starting materials are more especially those in which the residues $R_1$ and $R_2$ (formula V) are linked together. It goes without saying that with starting materials that give rise to extremely highly tensioned cyclic systems, for example to a cyclobutine or cyclohexine ring, the fragmentation of this invention cannot or can only restrictedly be carried out.

The iminoaziridine derivatives to be used as starting materials are derived from aminoaziridines of the general formula

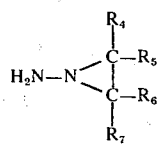

in which at least one of the residues $R_{4-7}$ represents a cycloalkyl residue, preferably the cyclopentyl, cyclohexyl or tetrahydronaphthalene residue, an aryl residue, such as a phenyl residues which may be substituted by halogen atoms, such as chlorine or bromine atoms, or by lower alkyl such as methyl or ethyl or phenyl residues, for example the phenyl, p-chlorophenyl or biphenyl residue, or in which $R_4$ or $R_5$ is linked with $R_6$ or $R_7$, for example through an alkylene residue with 3 to 5 carbon atoms, which may also carry a fused-on phenylene residue, and the others represent hydrogen atoms. Particularly suitable aminoaziridines are the 2-phenyl-aziridine, 2,3-diphenylaziridine or their p-chloro or p-bromo derivatives, the 2-tetrahydronaphthalene-, 2,3-butylene(1',4')- or 2,3-[2',3'-benzobutylene(1',4')]-1-amino-aziridine.

The fragmentation according to this invention can be achieved thermally or photochemically, in certain cases even at room temperature. The reaction may be conducted in an organic solvent such as a hydrocarbon, mineral oil, ether, phenol, dimethylformamide or other dialkylformamide, or in dimethylsulphoxide.

In certain cases the decomposition and the fragmentation are extremely easy to achieve. Thus, it is possible for the starting materials often to decompose in the desired manner even under the conditions of their formation. Therefore, the present invention includes also those variants of the present process in which the starting materials are formed in situ.

Most of the compounds obtained by the process of this invention are known and have as such valuable industrial or physiological properties and may be used as they are for a variety of purposes or they may be used as starting materials or intermediates in the manufacture of known or new industrially valuable organic compounds.

The process of this invention may be applied in the most varied spheres of organo-chemical industry. For example, with the aid of this process it is possible to manufacture aldehyde-acetylene compounds which were in the past only accessible with difficulty.

Most of the starting materials used in the present process are new; they may be prepared by known methods. Thus, the aminoaziridines may be reacted with the epoxyketones in the usual manner to form the imino compounds. The aminoaziridines in turn are likewise accessible by known methods.

The following Examples illustrate the invention.

EXAMPLE 1

152 mg of 1,2-epoxy-1-propionyl-cyclohex-4-ene, 5 ml of ether, 162 mg of 1-amino-2-phenylaziridine and 30 ml of glacial acetic acid are mixed at 0°C and stirred for 3 hours at 0°C. The reaction solution is poured into a solution of sodium bicarbonate, taken up in ether, the ethereal solution is washed neutral with water, dried over sodium sulphate and the ether is evaporated, to yield 290 mg of a crude product whose infrared spectrum contains no C=O-band.

100 mg of this product are slowly heated in a ball tube under 11 mm Hg pressure. At about 118°C decomposition sets in, becomes much stronger between 130° and 140°C and furnishes 45 mg of a distillate consisting of a 1:1-mixture of styrene and an aldehyde mixture. The latter consists mainly of non-2-en-6-in-1-al and little non-3-en-6-in-1-al, which are separated by gas chromatography.

The 1-amino-phenylaziridine used as starting material may be prepared thus:

A solution of 45.6 g of phenylethyleneglycol in 110 ml of pyridine is slowly mixed at 0°C with 56.4 ml of methanesulphonylchloride and then stirred overnight at 0° to 5°C. For working up the reaction mixture it is poured over a mixture of 500 g of ice and 150 ml of concentrated hydrochloric acid, then taken up in methylenechloride, agitated with sodium bicarbonate solution and repeatedly with sodium chloride solution; the methylenechloride solution is dried over sodium sulphate and the methylenechloride is evaporated, to yield 75.3 g of pure crude product which solidifies rapidly and is recrystallized from methylenechloride+hexane to furnish 63.3 g of phenyleneglycol dimesylate melting at 89° – Σ°C. After repeated recrystallization from methylenechloride+hexane the melting point rises to 94° – 96°C.

While cooling with ice under nitrogen 4.41 g of the resulting dimesylate are slowly added to 2.82 ml of anhydrous hydrazine; the batch is kept for 2 days at room temperature, then the excess hydrazine and the styrene formed as a by-product are suctioned off under a high vacuum, and the residue is extracted with 5 portions of ether. Distillation in a ball tube furnishes 776 mg of 1-amino-2-phenylaziridine melting at 60°C under 0.01 mm Hg pressure.

Alternatively, 50 ml of hydrazine hydrate, 10 g of the dimesylate described above and 450 ml of pentane may be stirred for 20 hours at about 20°C under nitrogen, whereupon the pentane solution is separated and the hydrazine hydrate twice extracted with pentane. 2.2 ml of glacial acetic acid are then stirred into the combined pentane extracts, whereupon 1-amino-2-phenylaziridine acetate settles out. It is kept for 2 hours at −18°C, filtered and the residue is recrystallized from methylenechloride+ether+pentane. Yield: 67.6% of theory. The acetate thus obtained melts at 73° – 74°C.

EXAMPLE 2

115 mg of 1-formyl-1,2-epoxy-cyclopentane and 125 mg of 7-amino-7-aza-bicyclo[4.1.0]heptane in 5 ml of ether and 1 drop of glacial acetic acid are stirred for 30 minutes at room temperature. The reaction solution is poured into a sodium bicarbonate solution, extracted with ether and the ethereal extract is twice agitated with sodium chloride solution, dried over sodium sulphate and evaporated, to yield 180 mg of a crude hydrazone which was not purified. The fragmentation is performed in the preparative gas chromatograph. Apiezone-L $T^{col} = 170°$ injector temperature 245°C. Fragmentation takes place immediately. 20 mg of the hydrazone furnish about 3 mg of hex-5-in-1-al which is characterized by means of its infrared spectrum [bands at 3310, 2730, 2115, 1723 cm$^{-1}$].

The 1-formyl-1,2-epoxy-cyclopentane used as starting material may be prepared thus:

972 mg of 1-formyl-cyclopent-2-ene in 6 ml of methanol are mixed with 1.56 ml of perhydrol of 30% strength. The reaction mixture is kept for 2¼ hours at a constant pH value of 8 by means of N-sodium hyroxide solution, during which the temperature rises to 47°C. The reaction mixture is extracted with chloroform, the chloroform solution is agitated three times with ammonium sulphate solution, dried over magnesium sulphate and the chloroform is distilled through a Vigreux column. The simultaneous distillation of two exactly equal batches furnishes a total of 900 mg of 1-formyl-1,2-epoxy-cyclopentane boiling at 36°C under 11 mm Hg pressure.

7-Amino-7-aza-bicyclo[4.1.0]heptane may be prepared thus:

A solution of 17.4 g of hydroxyurethane in 300 ml of absolute ether is mixed at 0°C within 30 minutes with 36.6 g of 2-nitrobenzenesulphonylchloride; then a solution of 15.2 g of triethylamine in 250 ml of ether is added within 1 hour, the mixture is allowed to warm up to room temperature and stirred for 30 minutes at this temperature. The resulting suspension is agitated with 2 × 350 ml of N-hydrochloric acid and once with 350 ml of water, dried over sodium sulphate and concentrated in a rotary evaporator. The resulting crude product is recrystallized from methylenechloride+pentane. The resulting urethane melts at 87° – 89°C.

A solution of 12.8 g of 7-aza-bicyclo[4.1.0]heptane in 20 ml of anhydrous methylenechloride is cooled to 0°C and a solution of 18.4 g of the resulting urethane in 45 ml of anhydrous methylenechloride is dropped in within 3 hours; the reaction mixture is stirred for 1 hour at room temperature, diluted with methylenechloride and washed with 3 × 30 ml of ice water. The methylenechloride solution is dried over sodium sulphate, substantially concentrated in a rotary evaporator and diluted with ether. The precipitate is filtered off, the filtrate concentrated and the resulting oil is twice chromatographed on silica gel (Merck, 0.05 – 0.2 mm). A 1:1-mixture of benzene+ether elutes the urethane which distils at 80° – 90°C under 0.01 mm Hg pressure and melts at 48.5° – 52.5°C.

925 mg of this urethane in 35 ml of 20% potassium hydroxide solution are heated for 1 hour at 100°C, then cooled, and the reaction solution is saturated with sodium caustic potash and extracted 3 times with ether. The extracts are dried and concentrated in the cold. The residue is sublimed at room temperature under 0.04 mm Hg pressure, to yield colourless crystalline 7-amino-7-aza-bicyclo[4.1.0]heptane melting at 48° – 49°C.

EXAMPLE 3

A mixture of 378 mg of 2-methyl-2,3-epoxycyclohexan-1-one, 442 mg of 1-amino-2-phenylaziridine, 90 ml of glacial acetic acid and 10 ml of ether is stirred for 2½ hours at 0°C under nitrogen. The reaction solution is poured into an ice-cooled sodium bicarbonate solution, taken up in ether and the ethereal solution is repeatedly agitated with water, dried over sodium sulphate and evaporated, to yield 744 mg of a crude product which is chromatographed on 60times its own weight of silica gel.

303 mg of the resulting mixture are heated in a ball tube for 1 hour at 150°C under 60 mm Hg pressure, whereupon 217 mg of a colourless oil pass over, which is identified as a 1:1-mixutre of styrene and hept-5-in-1-al and is separated by preparative gas chromatography on Carbowax 20 M and Apiezone L. The 2,4-dinitrophenylhydrazone of the resulting aldehyde melts at 107° – 108°C. According to its IR, MS, NMR, melting point and mixed melting point the resulting aldehyde is identical with the hept-5-in-1-al prepared by a different method.

EXAMPLE 4

630 mg of 1-acetyl-1,2-epoxy-cyclopentane and 1.12 g of 1-amino-2-phenylaziridine in 20 ml of ether are stirred for 3 hours at 0°C, then diluted with ether, agitated with sodium bicarbonate solution and sodium chloride solution, the ethereal solution is dried over sodium sulphate and evaporated.

303 mg of the resulting product are heated for 1 hour at 150°C under 60 mm Hg pressure, during which 227.5 mg of a colourless oil pass over which is separated by preparative gas chromatography into styrene and hept-5-in-1-al. This aldehyde is identical with the hept-5-in-1-al obtained in Example 3.

The 1-acetyl-1,2-epoxy-cyclopentane used in this Example may be prepared thus:

A solution of 11.02 g of 1-acetyl-cyclopent-1-ene in 50 ml of methanol is cooled to −10°C and mixed with 28.8 ml of perhydrol within 5 minutes. In the course of 1 hour, while stirring and cooling, 8.25 ml of 6N-sodium hydroxide solution are added, the whole is stirred for ½ hour at room temperature, diluted with 125 ml of water and extracted with pentane. The pentane solution is washed neutral with sodium chloride solution and the pentane is distilled off through a Vigreux column. The residue is distilled under 10 mm Hg pressure, to yield 1-acetyl-1,2-epoxy-cyclopentane passing over at 62° – 63°C.

EXAMPLE 5

A mixture of 560 mg of 2,3-epoxy-cyclohexanone, 1.067 g of 1-amino-2-phenylaziridine and 20 ml of methylenechloride is stirred for 2½ hours at 0°C, then poured out over ice, taken up in ether and the ethereal solution is agitated with sodium bicarbonate solution and with water, dried over sodium sulphate, evaporated and chromatographed on 60times its own weight of silica gel. Elution furnishes a mixture of synand antiiminoaziridine. 286 mg thereof are heated for 1½ hours at 140°C under 60 mm Hg pressure, during which 182.2 mg of pyrolyzate pass over and, by preparative gas chromatography on Apiezone L furnishes in addition to styrene pure hex-5-in-1-al. Yield: 61.7% of theory.

EXAMPLE 6

Starting from the under-mentioned parent ketones and working as described in the preceding Examples there are obtained via the corresponding iminoaziridine the following aldehydes:

| Starting ketone | Final product |
| --- | --- |
| 3β-acetoxy-16α,17-oxido-20-oxo-Δ⁵-pregnene | 3β-acetoxy-16-oxo-16,17-seco-Δ⁵-pregnen-17(20)-ine; m.p.121–124°C, whose dimethylacetal melts at 132–133°C |
| 3-methoxy-16α,17α-oxido-20-oxo-Δ¹,³,⁵⁽¹⁰⁾-19-nor-pregnatriene | 3-methoxy-16-oxo-16,17-seco-Δ¹,³,⁵⁽¹⁰⁾-19-nor-pregnatriene-17(20)-ine [foam; IR bands at 3.42, 3.70, 5.81, 6.20, 6.30, 6.68, 8.10 and 9.67 μ) |
| 1-oxo-2α,3-oxido-17β-acetoxy-5α-androstane | 3-oxo-17β-acetoxy-2,3-seco-5α-androst-1-ine; m.p. 110°C |
| cedrenal | 1-(formylmethyl)-3-ethinyl-4,4,8-trimethyl-bicyclo[3.3.0]-octane |
| 2-n-pentyl-cyclopent-2-en-1-one | dec-4-in-1-al, b.p 40–42°/0.001 mm Hg |
| 2-hexyl-cyclopent-2-en-1-one | undec-4-in-1-al, b.p. 105°/10 mm |
| 2-butyl-cyclopent-2-en-1-one | non-4-in-1-al, b.p. 81–82°C/10mm |
| 2-heptyl-cyclopent-2-en-1-one | dodec-4-in-1-al, b.p. 56°C/0.1 mm |
| 2-decyl-cyclopent-2-en-1-one | pentadec-4-in-1-al, b.p. 88°C/0.001 mm Hg |
| 2-ethyl-cyclopent-2-en-1-one | hept-4-in-1-al, b.p. 88°C/45 mm |

I claim:

1. Process for the manufacture of an aldehyde of the formula

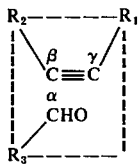

in which either $R_1$ and $R_3$ together represent alkylene with 2 or 3 chain carbon atoms, or $R_2$ and $R_3$ together represent alkylene with 3 or 4 chain carbon atoms and the remaining $R_2$ or $R_1$ is hydrogen or lower alkyl, which comprises condensing a compound of the formula

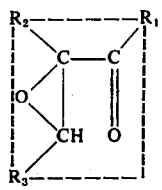

wherein $R_1$, $R_2$ and $R_3$ have the above meanings, with the aminoaziridine of the formula

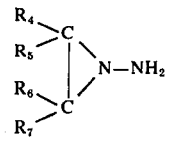

in which $R_4$, $R_5$, $R_6$ and $R_7$ each represents a member selected from hydrogen, lower alkyl, lower alkenyl, lower cycloalkyl, phenyl, tetrahydronaphthyl or phenyl substituted by at least one halogen, lower alkyl or phenyl, or $R_5$ and $R_6$ together are alkylene with 3 to 5 carbon atoms and $R_4$ and $R_7$ are hydrogen, at about room temperature and heating the condensation product to about 170° until the evolution of molecular nitrogen ceases.

2. Process as claimed in claim 1, wherein at least one of the radicals $R_4$, $R_5$, $R_6$ and $R_7$ stands for said cycloalkyl or phenyl radical and the other for hydrogen.

3. Process as claimed in claim 1, wherein $R_4$ stands for phenyl or phenyl substituted by at least one halogen, lower alkyl or phenyl and $R_5$, $R_6$ and $R_7$ represent hydrogen.

4. Process as claimed in claim 1, wherein $R_4$ represents phenyl, P-chlorophenyl, p-bromophenyl or biphenyl and $R_5$, $R_6$ and $R_7$ represent hydrogen.

5. Process according to claim 1, wherein $R_4$ stands for phenyl and $R_5$, $R_6$ and $R_7$ stand for hydrogen.

6. Process according to claim 1, wherein $R_4$ represents tetrahydronaphthyl and $R_5$, $R_6$ and $R_7$ represent hydrogen.

7. Process according to claim 1, wherein $R_5$ and $R_6$ represent phenyl, p-chloro-phenyl or p-bromo-phenyl and $R_4$ and $R_7$ stand for hydrogen.

8. Process according to claim 1, wherein $R_5$ together with $R_6$ is alkylene having 3 to 5 carbon atoms and $R_4$ and $R_7$ represent hydrogen.

9. Process according to claim 1, wherein $R_5$ together with $R_6$ is 1,4-butylene and $R_4$ and $R_7$ represent hydrogen.

10. Process as claimed in claim 1, wherein 1,2-epoxy-1-formyl-cyclopentane is used as starting material.

11. Process as claimed in claim 1, wherein 1,2-epoxy-1-acetyl-cyclopentane is used as starting material.

12. Process as claimed in claim 1, wherein 2-methyl-2,3-epoxy-cyclohexan-1-one is used as starting material.

13. Process as claimed in claim 1, wherein 2,3-epoxy-cyclohexanone is used as starting material.

* * * * *